(12) United States Patent
Zilla et al.

(10) Patent No.: US 11,471,187 B2
(45) Date of Patent: Oct. 18, 2022

(54) INVAGINATING DEVICE (71) Applicant: Strait Access Technologies Holdings (Pty) Ltd, Cape Town (ZA)

(72) Inventors: Peter Paul Zilla, Cape Town (ZA); Braden Sydney Clive Van Breda, Cape Town (ZA); Deon Bezuidenhout, Cape Town (ZA)

(73) Assignee: Strait Access Technologies Holdings (Pty) Ltd., Cape Town (ZA)

( * ) Notice: Subject to any disclaimer, the term of this patent is extended or adjusted under 35 U.S.C. 154(b) by 425 days.

(21) Appl. No.: 16/635,096

(22) PCT Filed: Jul. 10, 2018

(86) PCT No.: PCT/IB2018/055054
§ 371 (c)(1),
(2) Date: Jan. 29, 2020

(87) PCT Pub. No.: WO2019/038608
PCT Pub. Date: Feb. 28, 2019

(65) Prior Publication Data
US 2020/0170668 A1   Jun. 4, 2020

(30) Foreign Application Priority Data

Aug. 25, 2017  (GB) .................................... 1713711

(51) Int. Cl.
*A61B 17/34* (2006.01)
*A61B 17/22* (2006.01)
(52) U.S. Cl.
CPC .... *A61B 17/3421* (2013.01); *A61B 17/22032* (2013.01); *A61B 2017/3435* (2013.01)
(58) Field of Classification Search
CPC .......... A61B 17/3421; A61B 17/22032; A61B 17/3468; A61B 17/3435; A61F 2/958;
(Continued)

(56) References Cited

U.S. PATENT DOCUMENTS 5,045,070 A    9/1991  Grodecki
5,374,247 A *  12/1994 Lowery ............. A61M 25/0119
                                                    604/522

(Continued)

FOREIGN PATENT DOCUMENTS

DE    8323265    10/1985
WO    8801924    3/1988
WO    0191652    12/2001

OTHER PUBLICATIONS

Search Report and Written Opinion dated Dec. 3, 2018 in International Application Serial No. PCT/IB2018/055054.

*Primary Examiner* — Jocelin C Tanner
(74) *Attorney, Agent, or Firm* — Haugen Law Firm PLLP (57) ABSTRACT

An invaginating device includes an inner elongate member and an outer flexible tube with invaginated axial ends. The outer flexible tube is: disposed at a first axial end of the inner elongate member; concentric with the inner elongate member; sized to provide a radial gap there between; sealably connected at the axial ends of the outer flexible tube to the inner elongate member, with the axial spacing between such sealed axial ends being less than the axial length of the outer tube; and extendable to protrude from the first axial end of the inner elongate member and retractable to reduce such protrusion from the first axial end of the inner elongate member. Fluid contained within the radial gap defined between the inner elongate member and the outer flexible tube is either pressurized or a non-compressible fluid. An actuator is: movable relative to the inner elongate member; and engageable with the outer flexible tube to extend the outer flexible tube relative to the first axial end of the inner elongate member.

17 Claims, 8 Drawing Sheets

(58) Field of Classification Search
CPC ............... A61F 2/966; A61M 25/0119; A61M 2025/1065
See application file for complete search history.

(56) References Cited

U.S. PATENT DOCUMENTS

| | | | |
|---|---|---|---|
| 6,039,721 | A | 3/2000 | Johnson et al. |
| 6,200,288 | B1 | 3/2001 | Heaton et al. |
| 6,846,029 | B1* | 1/2005 | Ragner .................... B25B 9/00 294/219 |
| 8,109,895 | B2 | 2/2012 | Williams et al. |
| 2001/0044595 | A1 | 11/2001 | Reydel et al. |
| 2004/0169386 | A1* | 9/2004 | Shuttleworth ........ E01H 1/1206 294/137 |
| 2007/0213661 | A1 | 9/2007 | Gobel |
| 2011/0040365 | A1* | 2/2011 | Hirszowicz ...... A61B 17/22032 600/7 |
| 2013/0158590 | A1* | 6/2013 | Gui ...................... A61M 29/02 606/192 |
| 2014/0296831 | A1 | 10/2014 | Gobel |
| 2014/0336569 | A1 | 11/2014 | Gobel |

\* cited by examiner

INVAGINATING DEVICE

BACKGROUND

The present invention relates to an invaginating device. More particularly, the present invention relates to an invaginating device for use in surgical procedures.

Various invaginating devices are known. For instance:
US2007/0213661 "Closure system for managing rectal or anal incontinence", US2014/0296831 "Trans-anal inflow catheter and method for intermittently triggering a reflex-coordinated defecation" and US2014/0336569 "Device for trans-anal drainage of stool from the rectum of a patient and/or for the trans-anal application of inflowing liquid through a catheter-like element" describe devices that include:
an inner elongate member;
an outer flexible tube that is concentric with the inner elongate member, but sized to
provide a radial gap there between; and
pressurised fluid/an incompressible fluid within the radial gap,
wherein the axial ends of the outer tube are sealably connected to the inner elongate member with the spacing between such sealed axial ends being less than the axial length of the outer tube. A drawback of these arrangements is that they do not include a mechanism to control relative axial movement between the outer tube and the inner elongate member.

U.S. Pat. No. 5,374,247 "Method of delivering a substance to a fallopian tube", U.S. Pat. No. 6,039,721 "Method and catheter system for delivering medication with an everting balloon catheter" and US2001/0044595 "Introducer apparatus with eversible sleeve" describe devices that include:
an inner elongate member;
an outer tube that is concentric with the inner elongate member;
a flexible tube that is connected at a first axial end to the inner elongate member and
at a second axial end to the outer tube,
whereby relative axial movement of the inner elongate member and the outer tube causes the flexible tube to invaginate. A drawback of these arrangements is that to pressurise the annular gap provided by the invaginated flexible tube, the inner elongate member and the outer tube must maintain an effective seal there between.

U.S. Pat. No. 8,109,895 "Intestinal sleeves and associated deployment systems and methods" describes a tube with an invaginated flexible tube therein, wherein pressurisation of the annular gap provided by the invaginated flexible tube causes the flexible tube to be deployed past the axial end of the tube. This deployment system does not include a mechanical mechanism to control invagination of the pressurised flexible tube.

WO01/91652 "An invaginator apparatus" describes an invaginated tube with its axial ends connected to each other, which tube invaginates to permit an object to travel axially through the invaginated tube. A drawback of this apparatus is that invaginating of the tube is not easily controlled. Instead, the tube invaginates in response to travel of objects axially there through.

It is an object of the present invention to provide an invaginating device that includes a mechanism for invagination of a flexible tube and wherein both axial ends of the flexible tube are sealably connected to an inner elongate member.

SUMMARY OF THE INVENTION

According to a preferred embodiment of the invention, there is provided an invaginating device that includes:
an inner elongate member;
an outer flexible tube with invaginated axial ends, which outer flexible tube is:
  disposed at or near a first axial end of the inner elongate member;
  concentric with the inner elongate member;
  sized to provide a radial gap between the inner elongate member and the outer flexible tube;
  sealably connected at the axial ends of the outer flexible tube to the inner elongate member, with the axial spacing between such sealed axial ends being less than the axial length of the outer tube; and
  extendable to protrude from the first axial end of the inner elongate member and retractable to reduce such protrusion from the first axial end of the inner elongate member;
fluid within the radial gap defined between the inner elongate member and the outer flexible tube, which fluid is either: (i) pressurized; or (ii) a non-compressible fluid; and
an actuator that is:
  movable relative to the inner elongate member; and
  engageable with the outer flexible tube to extend the outer flexible tube relative to the first axial end of the inner elongate member.

Typically, the outer flexible tube is sealed to the inner elongate member at points axially inwards of the first axial end of the inner elongate member.

The actuator may be engageable with the outer flexible tube to retract the outer flexible tube relative to the first axial end of the inner elongate member.

Generally, the actuator is a tube that extends radially around the inner elongate member and is movable axially relative to the inner elongate member.

Preferably, the actuator is secured to the outer flexible tube within a region not extending axially more than the following distance from axial mid-point of the outer flexible tube:

[axial spacing between the sealed ends of the outer flexible tube]/2

Optionally, a portion of the inner elongate member at its first axial end tapers towards the first axial end.

Generally, the inner radial surface of the actuator defines an annular groove, and the actuator is secured to the outer flexible tube via adhesive disposed within the annular groove defined by the actuator. Alternatively, the outer radial surface of the outer flexible tube defines an annular groove, and the actuator is secured to the outer flexible tube via adhesive disposed within the annular groove defined by the outer flexible tube.

Preferably, the actuator defines an aperture through its radial wall, in the vicinity of the annular groove defined by the outer flexible tube.

Typically:
the actuator is secured to the outer flexible tube at a point axially inwards of a first axial end of the actuator; and
the actuator is movable to a fully forward position, in which the entire axial length of the outer flexible tube is located within the axial length of the actuator, with the first axially end of the actuator extending axially beyond: (i) the first axial end of the inner elongate member; and (ii) the axial end of the outer flexible tube that is distal the inner elongate member when the outer flexible tube is in an extended position.

Optionally, a portion of the inner radial surface of the actuator at the first axial end of the actuator, is conical.

Generally, the inner elongate member is a tube that:
is closed at the first axial end; and
defines an aperture between the sealed axial ends of the outer flexible tube, which aperture permits fluid communication between the interior of the inner elongate member and the radial gap defined between the inner elongate member and the outer flexible tube, to vary the pressure of the fluid within the radial gap.

Preferably, the invaginating device further includes a handle and a lever at a second axial end of the inner elongate member, which lever effects movement of the actuator.

Typically, the invaginating device further includes means for maintaining pressure of non-compressible fluid within the radial gap defined between the inner elongate member and the outer flexible tube, which pressure maintaining means comprises a pump and a radially expansible tube communicating between the pump and the inner elongate member, which radially expansible tube can increase in diameter in sympathy with an increase in internal pressure thereby to attenuate variations in pressure.

Alternatively, the pressure maintaining means could include:
a toroid that radially surrounds the inner elongate member;
a tube that permits fluid communication between a radial innermost point of the toroid and the radial gap defined between the inner elongate member and the outer flexible tube,
in use, the toroid including compressed gas and a non-compressible fluid, wherein the volume of non-compressible fluid is more than the volume of compressed gas.

According to an alternative embodiment of the invention, there is provided an invaginating device that includes:
an inner elongate member;
an outer flexible tube with invaginated axial ends, which outer flexible tube is:
disposed at or near a first axial end of the inner elongate member;
concentric with the inner elongate member;
sized to provide a radial gap between the inner elongate member and the outer flexible tube;
sealably connected at the axial ends of the outer flexible tube to the inner elongate member, with the axial spacing between such sealed axial ends being less than the axial length of the outer tube; and
extendable to protrude from the first axial end of the inner elongate member and retractable to reduce such protrusion from the first axial end of the inner elongate member;
fluid within the radial gap defined between the inner elongate member and the outer flexible tube, which fluid is either: (i) pressurized; or (ii) a non-compressible fluid; and
an actuator that:
is movable relative to the inner elongate member; and
bears against, but is not connected to the outer flexible tube, thereby to permit relative movement between the outer flexible tube and the actuator in the region where the actuator bears against the outer flexible tube to extend and retract the outer flexible tube relative to the first axial end of the inner elongate member.

Furthermore, the first axial end of the inner elongate member may be tapered to exert a biasing force upon the outer flexible tube, and thereby to either extend or retract the outer flexible tube relative to the first axial end of the inner elongate member.

Typically, the invaginating device further includes a sleeve that:
extends from the actuator;
surrounds the radial outer periphery of the outer flexible tube; and
extends along at least a portion of the axial length of the outer flexible tube,
such that, as the actuator moves the outer flexible tube from a retracted position to an extended position, the sleeve inhibits buckling of the portion of the outer flexible tube about which the sleeve extends.

BRIEF DESCRIPTION OF THE DRAWINGS

The invention will now be described in more detail, by way of examples only, with reference to the accompanying drawings in which.

DESCRIPTION OF THE INVENTION

With reference to FIGS. 1 to 5 of the drawings, an invaginating device 10 according to a preferred embodiment of the invention is provided for ensheathing an object for extraction or relocation. The invaginating device 10 includes an inner elongate member 12, an outer flexible tube 14 and an actuator 16.

Figure 3:
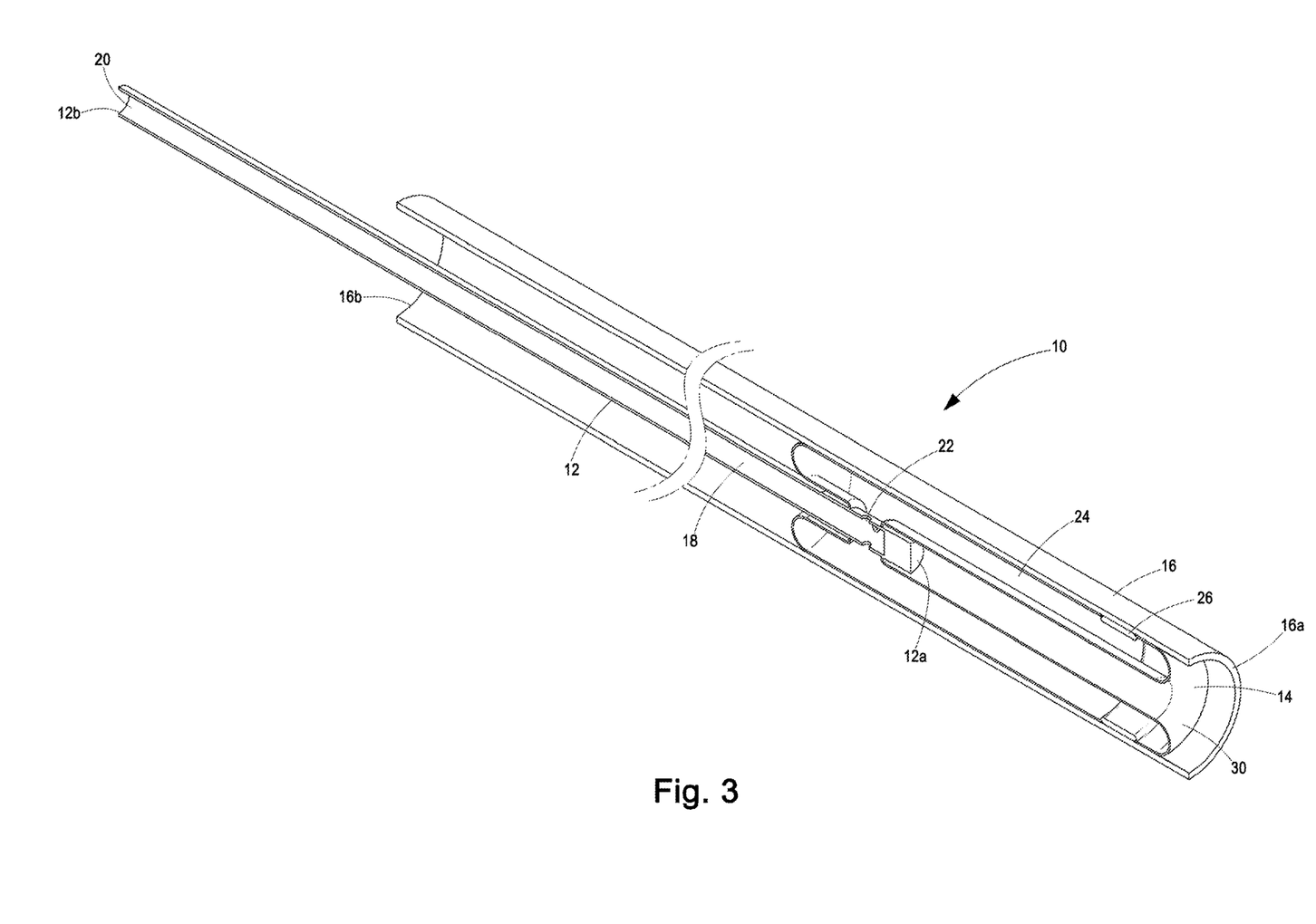
FIG. 3 is a perspective diametric cross-sectional view of the invaginating device in FIG. 1 with the flexible tube in the retracted position.
Figure 4:
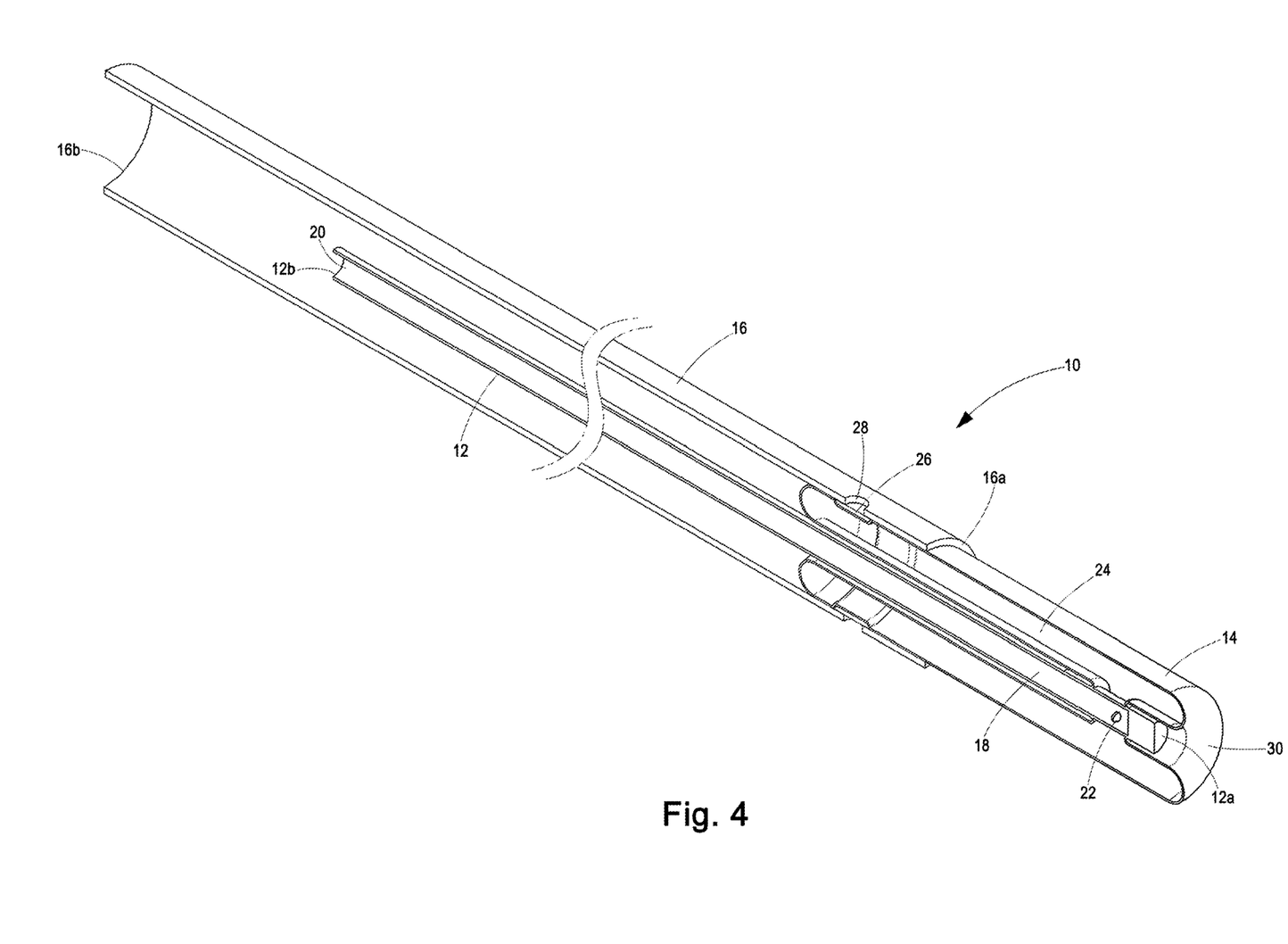
FIG. 4 is a perspective diametric cross-sectional view of the invaginating device in FIG. 1 with the flexible tube in the extended position.

Turning specifically to FIGS. 3 and 4, the inner elongate member 12 is an elongate hollow tube between 3 mm and 10 mm in outer diameter, which defines: (i) a central bore 18; (ii) a closed first axial end 12a; and (ii) a second axial end 12b. The tube 12 is sufficiently flexible, in use, to permit the tube 12 to be inserted into and pass along a non-linear artery, and sufficiently strong to resist hoop stresses resulting from pressurisation of the tube 12 bore 18. Preferably, the inner elongate member 12 is made of PEBAX(®) 72D. The inner elongate member 12 defines: an inlet 20 that permits fluid communication with the bore 18 at or near the second axial end 12b of the inner elongate member 12; and defines an outlet 22 that permits fluid communication with the bore 18 at or near the first axial end 12*a* of the inner elongate member 12. The inlet 20 is provided by an aperture defined by either the second axial end 12*b* of the inner elongate member 12 or the radial wall of the inner elongate member 12 near the second axial end 12*b* of the inner elongate member 12. The outlet 22 is provided by an aperture defined by either the first axial end 12*a* of the inner elongate member 12 or the radial wall of the inner elongate member 12 near the first axial end 12*a* of the inner elongate member 12. FIGS. 1 to 5 show the inlet 20 and outlet 22 defined by apertures in the radial wall of the inner elongate member 12. Although references are made to inlet 20 and outlet 22, it will be appreciated that, although: the inlet 20 permits fluid to enter the bore 18; and the outlet 22 permits fluid to exit the bore 18, during pressurisation of the invaginating device 10, during depressurisation of the invaginating device 10, the fluid flow is reversed, i.e.: the inlet 20 permits fluid to exit the bore 18; and the outlet 22 permits fluid to enter the bore 18.

Optionally, but not shown, the first axial end 12*a* of the inner elongate member 12 tapers towards the first axial end 12*a*.

The outer flexible tube 14 is made of a flexible material, such as PEBAX(®) 72D. The material from which the outer flexible tube 14 is made is more flexible and elastomeric than the material from which the inner elongate member 12 is made. Prior to assembly, the outer flexible tube 14 initially comprises a right circular cylindrical tube: between 3 mm and 10 mm in outer diameter; between 100 mm and 200 mm in axial length; and with an inner diameter greater than the outer diameter of the inner elongate member 12. However, during assembly of the invaginating device 10, the axial ends of the outer flexible tube 14 are invaginated inwards. In other words, the axial ends of the outer flexible tube 14 are deformed radially inwards and axially along the outer flexible tube 14. The axial ends of the outer flexible tube 14 (after invagination) are then sealably connected to the outer radial surface of the inner elongate member 12 at or near the first axial end 12*a* of the inner elongate member 12. The phrase "near the first axial end 12*a* of the inner elongate member 12" is intended to mean "a distance from the first axial end 12*a* of the inner elongate member 12 no greater than half the axial length of the outer flexible tube 14 (i.e. between 50 mm and 100 mm from the first axial end 12*a* of the inner elongate member 12)". Importantly, the sealed axial ends of the outer flexible tube 14 are axially spaced from each other, and the outlet 22 defined by the inner elongate member 12 is disposed between the sealed axial ends of the outer flexible tube 14. Although the sealed axial ends of the outer flexible tube 14 are axially spaced, the axial spacing between them is less than the axial length of the invaginated outer flexible tube 14. The outer flexible tube 14 and the inner elongate member 12 are generally concentric and are sized to define an annular gap 24 there between. This annular gap 24 is in fluid communication with the bore 18 defined by the inner elongate member 12 via the outlet 22. The outer flexible tube 14 is invaginatingly movable axially relative to the inner elongate member 12 so as to be extendable to protrude from the first axial end 12*a* of the inner elongate member 12 and retractable to reduce such protrusion from the first axial 12*a* end of the inner elongate member 12. More specifically, the outer flexible tube 14 is invaginatingly movable axially relative to the inner elongate member 12 between: (i) a retracted position, in which the outer flexible tube 14 is proximal the second axial end 12*b* of the inner elongate member 12 and the outer flexible tube 14 does not extend axially beyond the first axial end 12*a* of the inner elongate member 12; and (ii) an extended position, in which the outer flexible tube 14 is distal the second axial end 12*b* of the inner elongate member 12, extending axially beyond the first axial end 12*a* of the inner elongate member 12 by between 25 mm and 75 mm.

The actuator 16 comprises either a rod or a tube (as shown in FIGS. 1 to 5) located radially around the inner elongate member 12, which actuator is between 200 mm and 400 mm in axial length and defines first and second axial ends 16*a* and 16*b*, respectively. The actuator 16 extends along the inner elongate member 12 generally from near the second end 12*b* of the inner elongate member 12 to the outer flexible tube 14. The actuator 16 is connected to the inner elongate member 12 (by locating at least partially around the inner elongate member 12) and axially movable relative to the inner elongate member 12. Optionally, the actuator 16 is slidably connected to the inner elongate member 12 by a ring that extends around the radial outer surface of the inner elongate member 12 in the region of the second axial end 12*b* of the inner elongate member 12. The first axial end 16*a* of the actuator 16 is engageable with the outer flexible tube 14 to cause the outer flexible tube 14 to protrude from the first axial end 12*a* of the inner elongate member 12, and to cause the outer flexible tube 14 to retract and reduce such protrusion from the first axial 12*a* end of the inner elongate member 12. Preferably, the actuator 16 is engageable with the outer flexible tube 14 to cause the outer flexible tube 14 to move from the retracted position to the extended position and/or from the extended position to the retracted position. FIGS. 1 to 5 show the first axial end 16*a* of the actuator 16 adhered to the outer flexible tube 14 within a region not extending axially more than the following distance from axial mid-point of the outer flexible tube 14 (i.e. the axial midpoint of the outer flexible tube when the outer flexible tube 14 is in the unassembled condition, i.e. prior to invagination when the outer flexible tube 14 is right circular cylindrical in shape):

[axial spacing between the sealed ends of the outer flexible tube]/2

Optionally, the actuator 16 could be a sheath (e.g. an introducer sheath) through which the inner elongate member 12 (with outer flexible member 14) extends, which sheath frictionally engages the radial outer surface of the outer flexible member 14 to move the outer flexible member 14 between the retracted position and the extended position.

Figure 5:
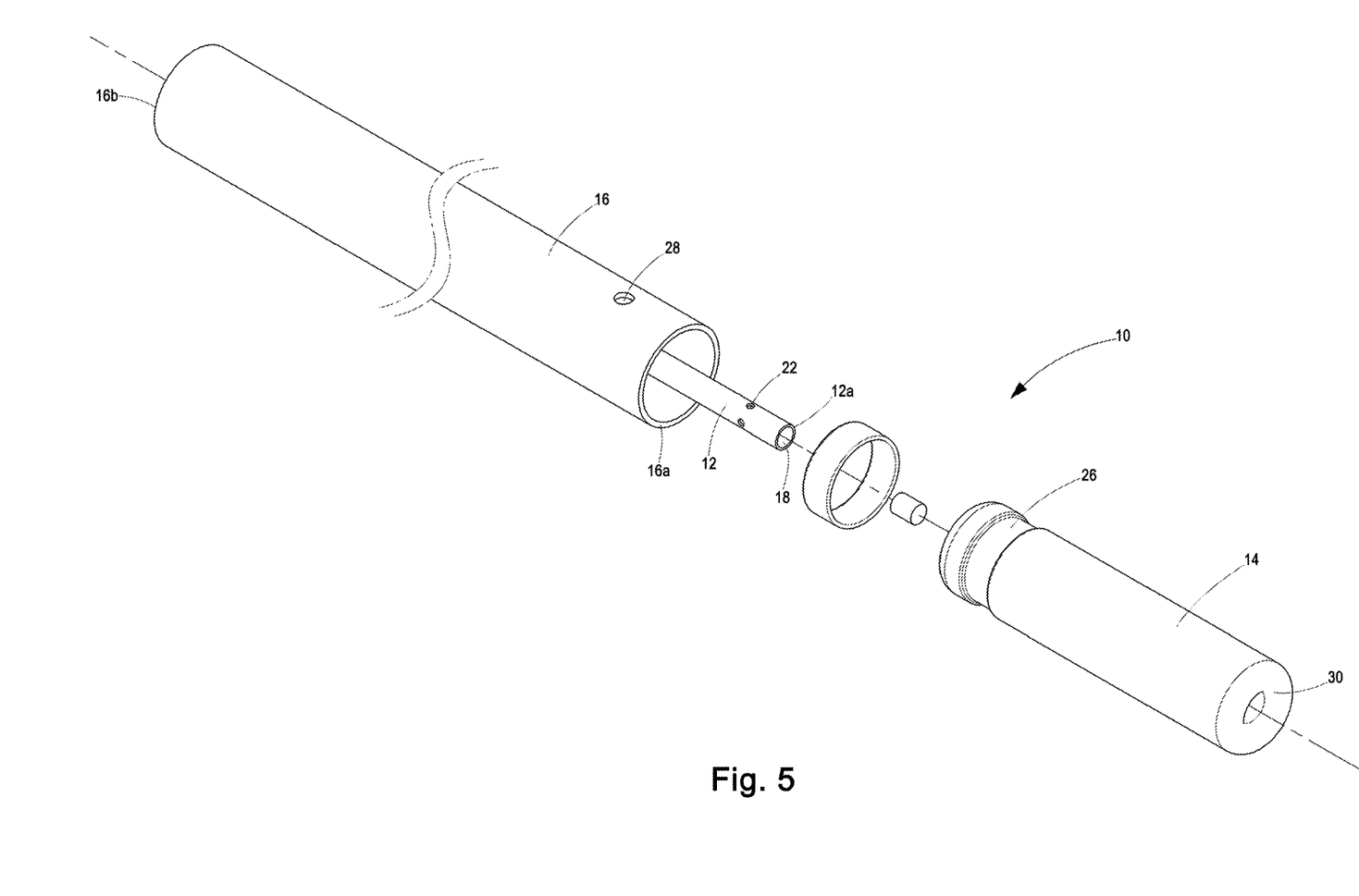
FIG. 5 is a perspective exploded view of the invaginating device in FIG. 1.

Referring specifically to FIGS. 3 to 5, the outer radial surface of the outer flexible tube 14 defines an annular groove 26, and the actuator 16 is secured to the outer flexible tube 14 via adhesive disposed within the annular groove 26 defined by the outer flexible tube 14. However, it will be appreciated that the inner radial surface of the actuator 16 could alternatively define an annular groove 26, and the actuator 16 could be secured to the outer flexible tube 14 via adhesive disposed within the annular groove 26 defined by the actuator 16.

Furthermore, the actuator 16 defines an aperture 28 through its radial wall, in the vicinity of the annular groove 26 defined by the outer flexible tube 14, through which aperture 28 adhesive is introduced into the annular groove 26.

It will also be appreciated that the actuator 16 is secured to the outer flexible tube 14 at a point axially inwards of the first axial end 16*a* of the actuator 16. This configuration enables:

(i) the entire axial length of the outer flexible tube 14 to be located radially within the actuator 16 (i.e.

ensheathed by the actuator 16) when the actuator is moved to a fully forward position most distal the second axial end 12b of the inner elongate member 12 (i.e. in which the outer flexible tube 14 is in the extended position); and (ii) the first axially end 16a of the actuator 16 to extend axially beyond: (a) the first axial end 12a of the inner elongate member 12; and (b) the axial end (shown as reference number 30 in FIGS. 2 and 4) of the invaginated outer flexible tube 14 that is distal the inner elongate member 12 when the outer flexible tube 14 is in the extended position.

Optionally, but not shown, a portion of the inner radial surface of the actuator 16 at the first axial end 16a of the actuator 16, is conical. This conical inner radial surface optionally coupled with the tapered first end 12a of the inner elongate member 12 act to bias the outer flexible tube towards the extended position.

Figure 1:
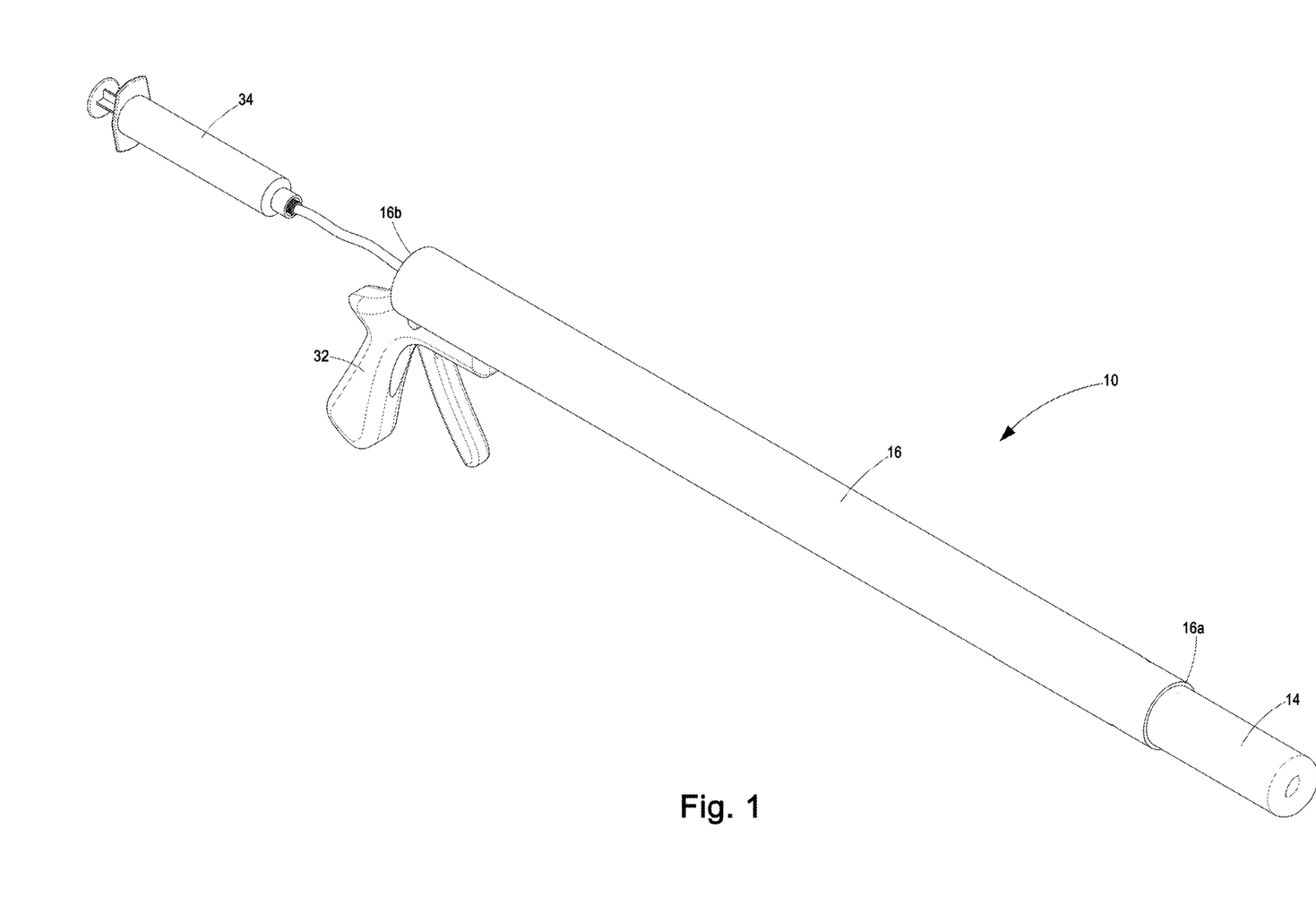
FIG. 1 is a perspective view of an invaginating device according to a preferred embodiment of the invention, with the flexible tube in a retracted position.
Figure 2:
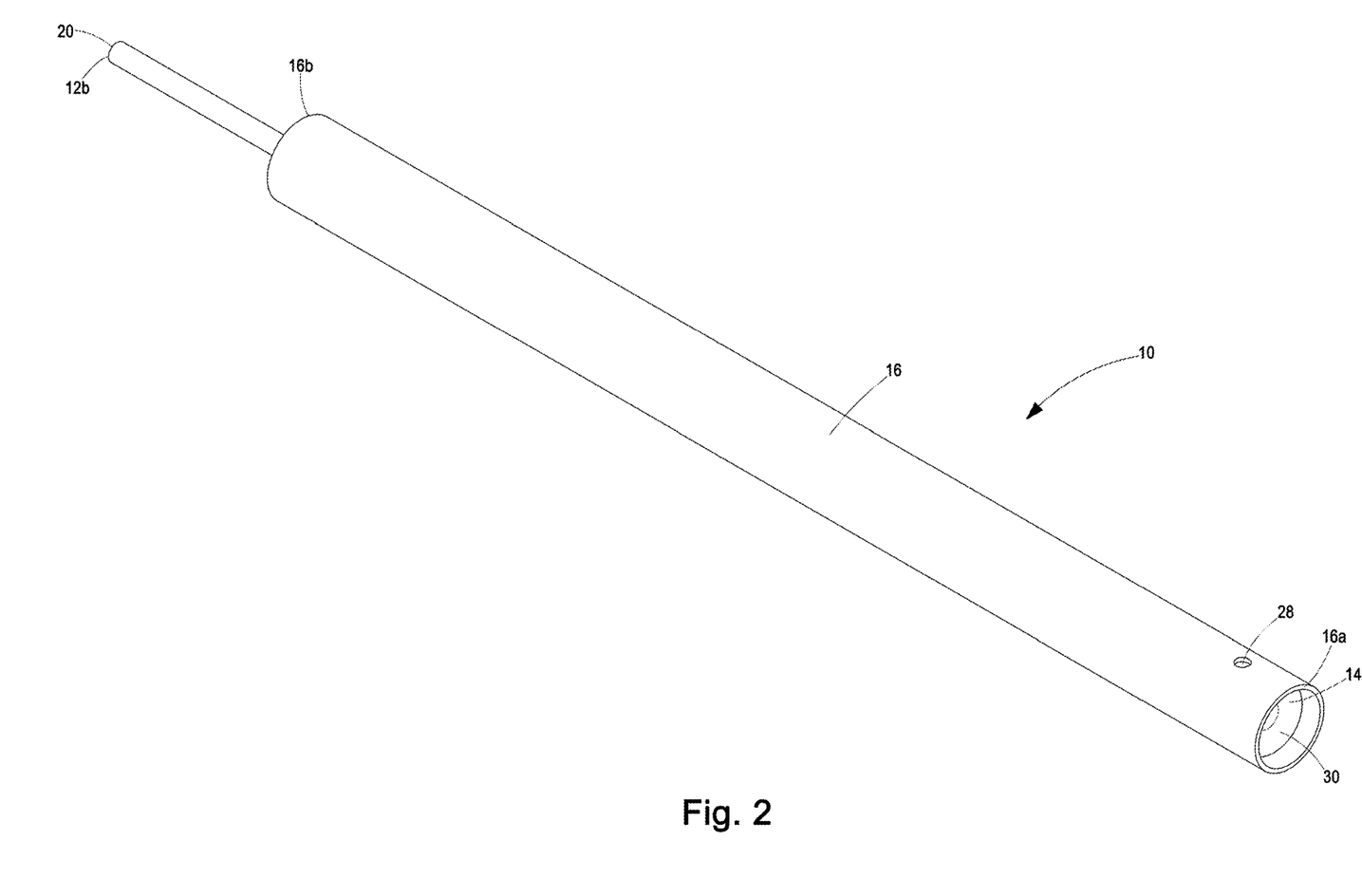
FIG. 2 is a perspective view of the invaginating device in FIG. 1 with the flexible tube in an extended position.

Referring to FIG. 1, a handle and lever 32 are disposed at or near the second axial end 12b of the inner elongate member 12, which lever 32 effects movement of the actuator 16, in turn to cause the outer flexible tube 14 to move between the retracted and extended positions.

Remaining with FIG. 1, a pressure regulator 34 is also disposed at or near the second axial end 12b of the inner elongate member 12. The pressure regulator 34 is shown in the form of a syringe that is filled with a fluid. The pressure regulator 34 is in fluid communication with the annular gap 24 between the inner elongate member 12 and the outer flexible tube 14 via the bore 18 and the outlet 22 (both defined by the inner elongate member 12). A variation in pressure within the pressure regulator 34, varies the pressure within the bore 18 and the pressure within the annular gap 24 between the inner elongate member 12 and the outer flexible tube 14. In use, the pressure regulator 34 pressurises the annular gap 24 between the inner elongate member 12 and the outer flexible tube 14, thereby to induce tension within the outer flexible tube 14. This tension inhibits buckling of the outer flexible tube 14 during movement between the retracted position and the extended position. Depending on the application, the annular gap 24 between the inner elongate member 12 and the outer flexible tube 14 may be filled with a pressurized fluid (such as a pressurized gas), or with a non-compressible fluid (e.g. a liquid).

In use:
- a first axial end of the invaginating device 10 is inserted into an artery;
- the first end 12a of the inner elongate member 12 is moved along the artery towards an object to be captured/relocated;
- with the first end 12a of the inner elongate member 12 adjacent the object to be captured, the lever 32 is operated to cause the actuator 16 to move axially along the inner elongate member 12 towards the first axial end 12a of the inner elongate member 12 and thereby cause the outer flexible tube 14 to move from the retracted position to the extended position. While moving towards the extended position, the outer flexible tube 14 ensheaths the object;
- the actuator 16 may be full extended similarly to cover the object radially, forcing the outer flexible tube 14 radially inwards further to compress the object;
- the invaginating device 10, with the object captured within the outer flexible tube 14 is then: (i) remove from the artery; or (ii) relocated along the artery, being released by moving the outer flexible tube 14 to the retracted position. During such removal, the outer flexible tube 14 cushions and protects the object captured thereby. Furthermore, invaginating movement of the outer flexible tube 14 does not induce sheer stresses between the outer flexible tube 14 and the object captured thereby during protrusion and retraction of the outer flexible tube 14 relative to the first axial end 12a of the inner elongate member 12.

It will be appreciated that movement of the outer flexible tube 14 over an object to be ensheathed thereby may cause a variation in volume of fluid within the annular gap 24 between the inner elongate member 12 and the outer flexible tube 14, which change in volume may, in turn, cause a variation in pressure within the fluid. To dampen fluctuations in fluid pressure within the annular gap 24 (and thereby reduce the risk of failure of the outer flexible tube 14), a pressure maintaining means may be disposed between the pressure regulator 34 and the bore 18 defined by the inner elongate member 12. The pressure maintaining means 36 comprises a pump (not shown) and a radially expansible tube (not shown) communicating between the pump and the inner elongate member 12, which radially expansible tube can increase in diameter in sympathy with an increase in internal pressure thereby to attenuate variations in pressure.

Figure 6:
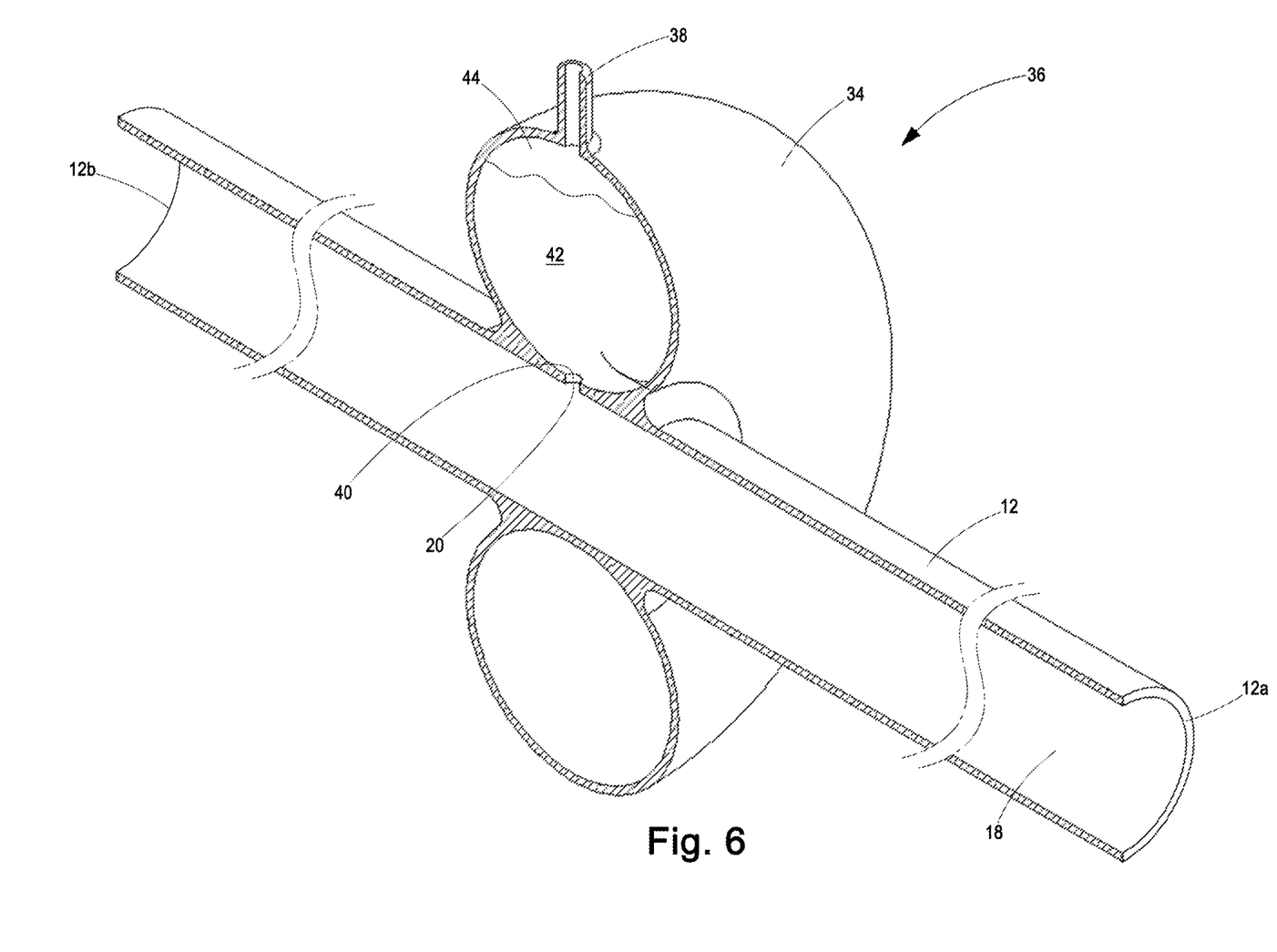
FIG. 6 is a perspective diametric cross-sectional view of a pressure maintaining means for use with the invaginating device in FIG. 1.

Alternatively, with reference to FIG. 6, the pressure maintaining means 36, could be in the form of a toroid that radially surrounds the inner elongate member 12. The toroid defines a toroid inlet 38 that is in fluid communication with the pressure regulator 34 and a toroid outlet 40 that is in fluid communication with the bore 18 defined by the inner elongate member 12 via the inlet 20 defined by the inner elongate member 12. The toroid outlet 40 is located at a radial innermost point of the toroid 36. In use, the toroid 36 includes compressed gas 42 and a non-compressible fluid 44, wherein the volume of non-compressible fluid 44 within the toroid 36 is more than the volume of compressed gas 42 within the toroid 36. Typically, the ratio of non-compressible fluid volume to compressed gas volume is greater than two-thirds. This ensures that, irrespective of the orientation of the invaginating device 10, the compressed gas 42 does not enter the bore 18 via the toroid outlet 40.

Figure 7:
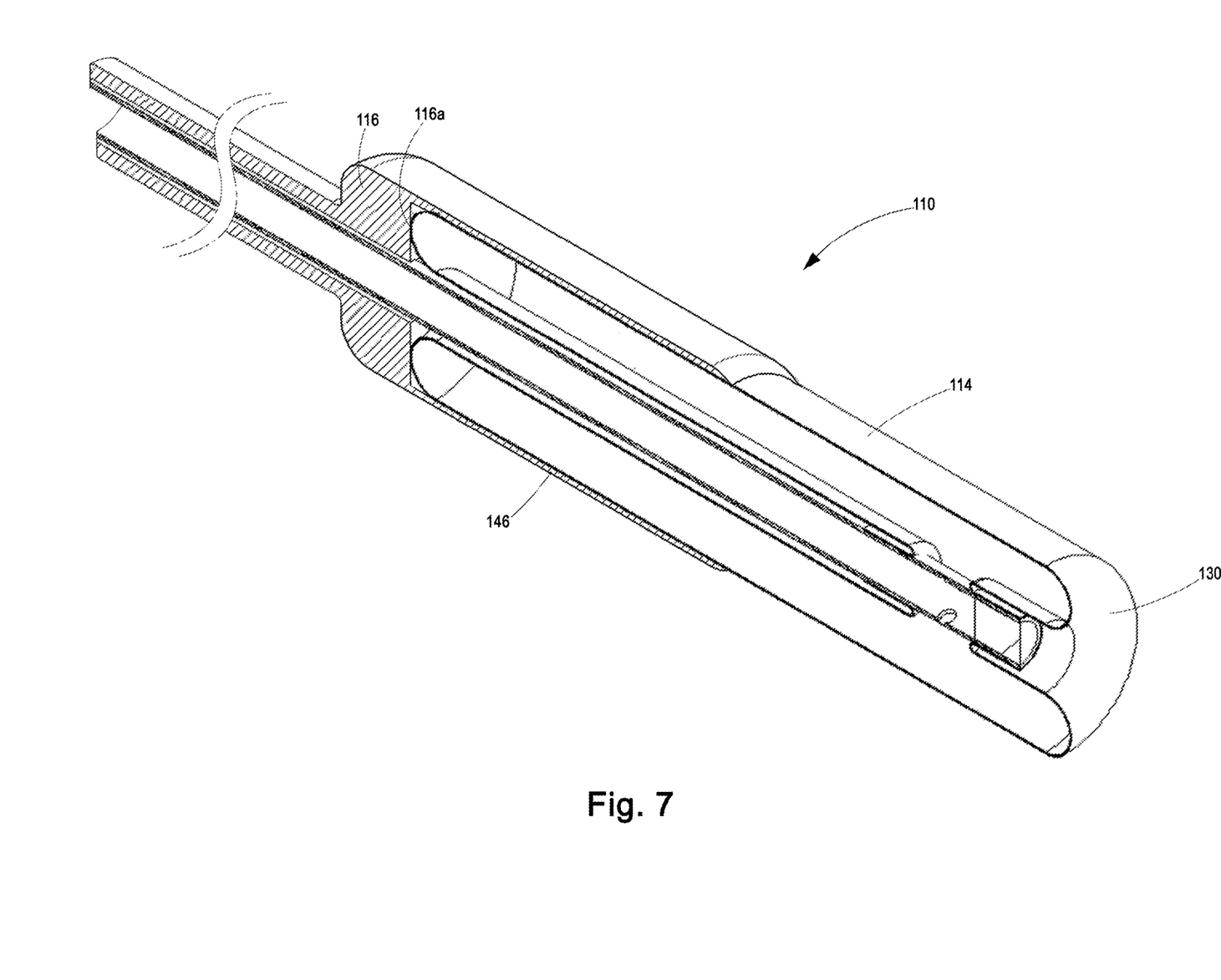
FIG. 7 is a perspective diametric cross-sectional view of an invaginating device according to an alternative embodiment of the invention, with the flexible tube in the retracted position.
Figure 8:
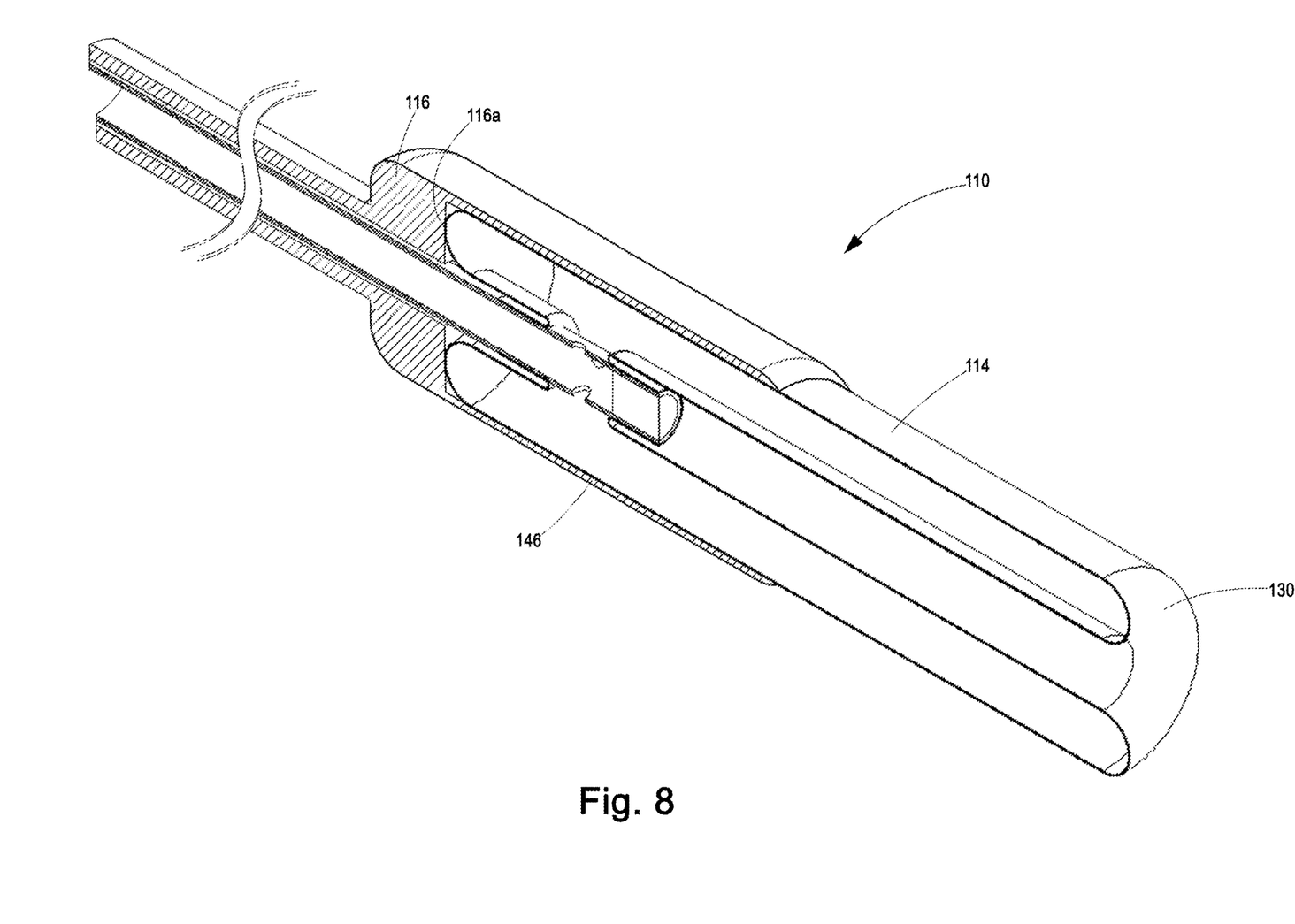
FIG. 8 is a perspective diametric cross-sectional view of the invaginating device in FIG. 5, with the flexible tube in the extended position.

FIGS. 7 and 8 show an alternative embodiment of the invaginating device 110. In this embodiment, the actuator 116 is not connected to the radial outer surface of the outer flexible tube 114. Instead, the first axial end 116a of the actuator 116 bears against an axial portion of the invaginated outer flexible tube 114. Importantly, the actuator 116 is not secured to the outer flexible tube 114, thereby permitting relative sliding between the outer flexible tube 114 and the first axial end 116a of the actuator 116 as the actuator 116 pushes the outer flexible tube 114 from the retracted position to the extended position. A sleeve 146 extends axially from the first axial end 116a of the actuator 116 and is sized and shaped to surround the radial outer periphery of the outer flexible tube 114. The sleeve 146 could extend along only a portion of the axial length of the invaginated outer flexible tube 114 or it could extend along the entire axial length of the invaginated outer flexible tube 114. Since the sleeve 146 is attached to the actuator 116, which actuator 116 does not extend beyond the axial end of the invaginated outer flexible tube 114 against which the first axial end 116a of the actuator 116 bears, the sleeve 146 does not protrude beyond the other axial end 130 of the invaginated outer flexible tube 114 as the outer flexible tube 114 is moved from the retracted position to the extended position. By restricting radial expansion of the outer flexible tube 114 during movement of the outer flexible tube 114 from the retracted position to the extended position, the sleeve 146 acts to increase the buckling resistance of the outer flexible tube 114 within the region of the outer flexible tube 114 about which the sleeve 146 extends.

Optionally, the first end 112a of the inner elongate member 12 is tapered to bias the outer flexible tube 114 towards the retracted position.

By providing an actuator 16 and 116 for controlling movement of the outer flexible tube 14 and 114 between the retracted position and the extended position, the invaginating device 10 is specifically suited to capture objects for extraction from an artery/relocation within an artery. Furthermore, by sealably connecting the axial ends (when in the unassembled state) of the outer flexible tube 14 and 114 to the inner elongate member 12 and 112, with the outlet 22 defined by the inner elongate member 12 disposed between such sealed axial ends, the actuator 16 and 116 need not be sealed to the inner elongate member 12 and 112 to maintain pressure in the fluid within the annular gap 24 defined between the outer flexible tube 14 and 114 and the inner elongate member 12 and 112.

The invention claimed is:

1. An invaginating device including:
   an inner elongate member;
   an outer flexible tube with invaginated axial ends, which outer flexible tube defines an inner radial surface and an outer radial surface, wherein the inner radial surface is sealably connected at the axial ends of the outer flexible tube to an outer radial surface of the inner elongate member, with an axial spacing between such sealed ends being less than the axial length of the outer flexible tube, and wherein the outer flexible tube is:
      disposed at or near a first axial end of the inner elongate member;
      concentric with the inner elongate member;
      sized to provide a radial gap between the inner elongate member and the outer flexible tube; and
      extendable to protrude from the first axial end of the inner elongate member and retractable to reduce such protrusion from the first axial end of the inner elongate member;
   fluid within the radial gap defined between the inner elongate member and the outer flexible tube, which fluid is either: (i) pressurized; or (ii) a non-compressible fluid; and
   an actuator that is:
      movable relative to the inner elongate member; and
      engageable with the outer flexible tube to extend the outer flexible tube relative to the first axial end of the inner elongate member,
   characterised in that:
      the inner elongate member is a tube that:
         is closed at the first axial end; and
         defines an aperture between the sealed axial ends of the outer flexible tube, which aperture permits fluid communication between an interior of the inner elongate member and the radial gap defined between the inner elongate member and the outer flexible tube, to vary pressure of the fluid within the radial gap.

2. An invaginating device according to claim 1, wherein the outer flexible tube is sealed to the inner elongate member at points axially inwards of the first axial end of the inner elongate member.

3. An invaginating device according to claim 2, wherein the actuator is engageable with the outer flexible tube to retract the outer flexible tube relative to the first axial end of the inner elongate member.

4. An invaginating device according to claim 3, wherein the actuator is a tube that extends radially around the inner elongate member and is movable axially relative to the inner elongate member.

5. An invaginating device according to claim 4, wherein the actuator is secured to the outer flexible tube within a region not extending axially more than the following distance from axial mid-point of the outer flexible tube:

[axial spacing between the sealed ends of the outer flexible tube]/2.

6. An invaginating device according to claim 5, wherein a portion of the first axial end of the inner elongate member tapers towards the first axial end.

7. An invaginating device according to claim 6, wherein the actuator defines an inner radial surface, which inner radial surface of the actuator defines an annular groove, and the actuator is secured to the outer flexible tube via adhesive disposed within the annular groove defined by the actuator.

8. An invaginating device according to claim 6, wherein the outer radial surface of the outer flexible tube defines an annular groove, and the actuator is secured to the outer flexible tube via adhesive disposed within the annular groove defined by the outer flexible tube.

9. An invaginating device according to claim 8, wherein the actuator defines an aperture through its radial wall, in the vicinity of the annular groove defined by the outer flexible tube.

10. An invaginating device according to claim 9, wherein:
    the actuator is secured to the outer flexible tube at a point axially inwards of a first axial end of the actuator; and
    the actuator is movable to a fully forward position, in which the entire axial length of the outer flexible tube is located within the axial length of the actuator, with the first axial end of the actuator extending axially beyond: (i) the first axial end of the inner elongate member; and (ii) the axial end of the outer flexible tube that is distal the inner elongate member when the outer flexible tube is in an extended position.

11. An invaginating device according to claim 10, wherein a portion of the inner radial surface of the actuator at the first axial end of the actuator, is conical.

12. An invaginating device according to claim 11, further including a handle and a lever at a second axial end of the inner elongate member, which lever effects movement of the actuator.

13. An invaginating device according to claim 12, further including means for maintaining pressure of non-compressible fluid within the radial gap defined between the inner elongate member and the outer flexible tube, which pressure maintaining means comprises a pump and a radially expansible tube communicating between the pump and the inner elongate member, which radially expansible tube can increase in diameter in sympathy with an increase in internal pressure thereby to attenuate variations in pressure.

14. An invaginating device according to claim 12, further including means for maintaining pressure of non-compressible fluid within the radial gap defined between the inner elongate member and the outer flexible tube, which pressure maintaining means includes:
    a toroid that radially surrounds the inner elongate member;
    a tube that permits fluid communication between a radial innermost point of the toroid and the radial gap defined between the inner elongate member and the outer flexible tube, in use, the toroid including compressed gas and a non-compressible fluid, wherein the volume of non-compressible fluid is more than the volume of compressed gas.

15. An invaginating device according to claim 2, wherein the actuator bears against, but is not connected to the outer flexible tube, thereby to permit relative movement between the outer flexible tube and the actuator in the region where the actuator bears against the outer flexible tube.

16. An invaginating device according to claim 2, wherein the first axial end of the inner elongate member is tapered to exert a biasing force upon the outer flexible tube, and thereby to either extend or retract the outer flexible tube relative to the first axial end of the inner elongate member.

17. An invaginating device according to claim 16, further including a sleeve that:
- extends from the actuator;
- surrounds the radial outer surface of the outer flexible tube; and
- extends along at least a portion of the axial length of the outer flexible tube, such that, as the actuator moves the outer flexible tube between a retracted position and an extended position, the sleeve inhibits buckling of the portion of the outer flexible tube about which the sleeve extends.

\* \* \* \* \*